United States Patent
Blacquiere et al.

(10) Patent No.: US 7,544,837 B2
(45) Date of Patent: Jun. 9, 2009

(54) BASE METAL DEHYDROGENATION OF AMINE-BORANES

(75) Inventors: Johanna Marie Blacquiere, Ottawa (CA); Richard Jeffrey Keaton, Pearland, TX (US); Ralph Thomas Baker, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 15 days.

(21) Appl. No.: 11/590,136

(22) Filed: Oct. 30, 2006

(65) Prior Publication Data

US 2007/0128475 A1 Jun. 7, 2007

Related U.S. Application Data

(60) Provisional application No. 60/733,836, filed on Nov. 4, 2005.

(51) Int. Cl.
*B01J 7/00* (2006.01)
*C01B 3/02* (2006.01)

(52) U.S. Cl. .................. 564/9; 423/297; 423/284; 423/285; 564/10; 564/11; 48/61

(58) Field of Classification Search .......... 423/284, 423/285, 297; 564/9, 10, 11; 48/61
See application file for complete search history.

(56) References Cited

U.S. PATENT DOCUMENTS

| | | | | |
|---|---|---|---|---|
| 3,024,240 | A * | 3/1962 | Hough | 546/13 |
| 3,151,168 | A * | 9/1964 | McElroy et al. | 568/3 |
| 4,315,786 | A | 2/1982 | English et al. | |
| 4,381,206 | A | 4/1983 | Grant et al. | |
| 4,468,263 | A | 8/1984 | Artz et al. | |
| 4,673,528 | A | 6/1987 | Artz et al. | |
| 4,801,439 | A * | 1/1989 | Blum et al. | 423/284 |
| 5,618,435 | A * | 4/1997 | Fehlner et al. | 210/651 |
| 6,534,033 | B1 | 3/2003 | Amendola et al. | |
| 6,683,025 | B2 | 1/2004 | Amendola et al. | |
| 7,285,142 | B1 * | 10/2007 | Mohajeri et al. | 48/61 |
| 7,316,788 | B2 * | 1/2008 | Autrey et al. | 252/182.34 |
| 2003/0157018 | A1 * | 8/2003 | Zaluski et al. | 423/648.1 |
| 2005/0142404 | A1 * | 6/2005 | Boucher et al. | 429/20 |
| 2005/0180916 | A1 * | 8/2005 | Autrey et al. | 423/658.2 |
| 2005/0191236 | A1 * | 9/2005 | Pinkerton et al. | 423/658.2 |
| 2006/0194702 | A1 * | 8/2006 | Alberti et al. | 508/234 |
| 2006/0225350 | A1 * | 10/2006 | Spallone et al. | 48/198.2 |
| 2006/0287521 | A1 * | 12/2006 | Davis, Jr. | 540/541 |
| 2006/0292068 | A1 * | 12/2006 | Stephens et al. | 423/648.1 |
| 2007/0039474 | A1 * | 2/2007 | Narula et al. | 96/108 |
| 2007/0128475 | A1 * | 6/2007 | Blacquiere et al. | 429/13 |
| 2007/0183967 | A1 * | 8/2007 | Thorn et al. | 423/648.1 |
| 2007/0189950 | A1 * | 8/2007 | Thorn et al. | 423/285 |

OTHER PUBLICATIONS

Jaska et al. Transition Metal-Catalyzed Formation of Boron-Nitrogen Bonds: Catalytic Dehydrocoupling of Amine-Borane Adducts to Form Aminoboranes and Borazines. JACS 125(31) 2003 9424-34.*
Jaska et al. Phosphorus, Sulfur and Silicon 179:733-736, 2004.*
Blythas et al. JAOCS Apr. 11, 1962 vol. 84No. 7 pp. 1075-2468.*
Amendola et al. Jour. Power Sources 85(2000) 186-189.*
Wang et al. Inorg.Chim.Acta, 148 (1988) 185-190.*
Couturier et al. Org. Letters 2001 vol. 3 No. 3 465-467.*
Amendola et al. Hydrogen Energy. Intl Jour Hydrogen energy (2000) 969-975.*
Myneni et al. (ed). First Intl Workshop of Hydrogen in Materials and Vacuum Systems. Am Inst Physics vol. 671 Nov. 2002 12 pages.*
Jaska et al., "Transition Metal-Catalyzed Formation of Boron-Nitrogen Bonds: Catalytic Dehydrocoupling of Amine-Borane Adducts to Form Aminoboranes and Borazines." JACS vol. 125 (Jul. 2003) pp. 9424-9434.
Temple et al., "Catalytic Dehydrocoupling of Amine-Borane Adducts to Form Aminoboranes and Borazines." Phosphorus, Sulfer and Silicon, and the Related Elements, vol. 179 (Apr. 2004) pp. 733-736.

* cited by examiner

*Primary Examiner*—Peter G O'Sullivan
(74) *Attorney, Agent, or Firm*—Robert P. Santandrea; Juliet A. Jones

(57) ABSTRACT

A method of dehydrogenating an amine-borane having the formula $R^1H_2N$—$BH_2R^2$ using base metal catalyst. The method generates hydrogen and produces at least one of a $[R^1HN$—$BHR^2]_m$ oligomer and a $[R^1N$—$BR^2]_n$ oligomer. The method of dehydrogenating amine-boranes may be used to generate $H_2$ for portable power sources, such as, but not limited to, fuel cells.

13 Claims, 1 Drawing Sheet

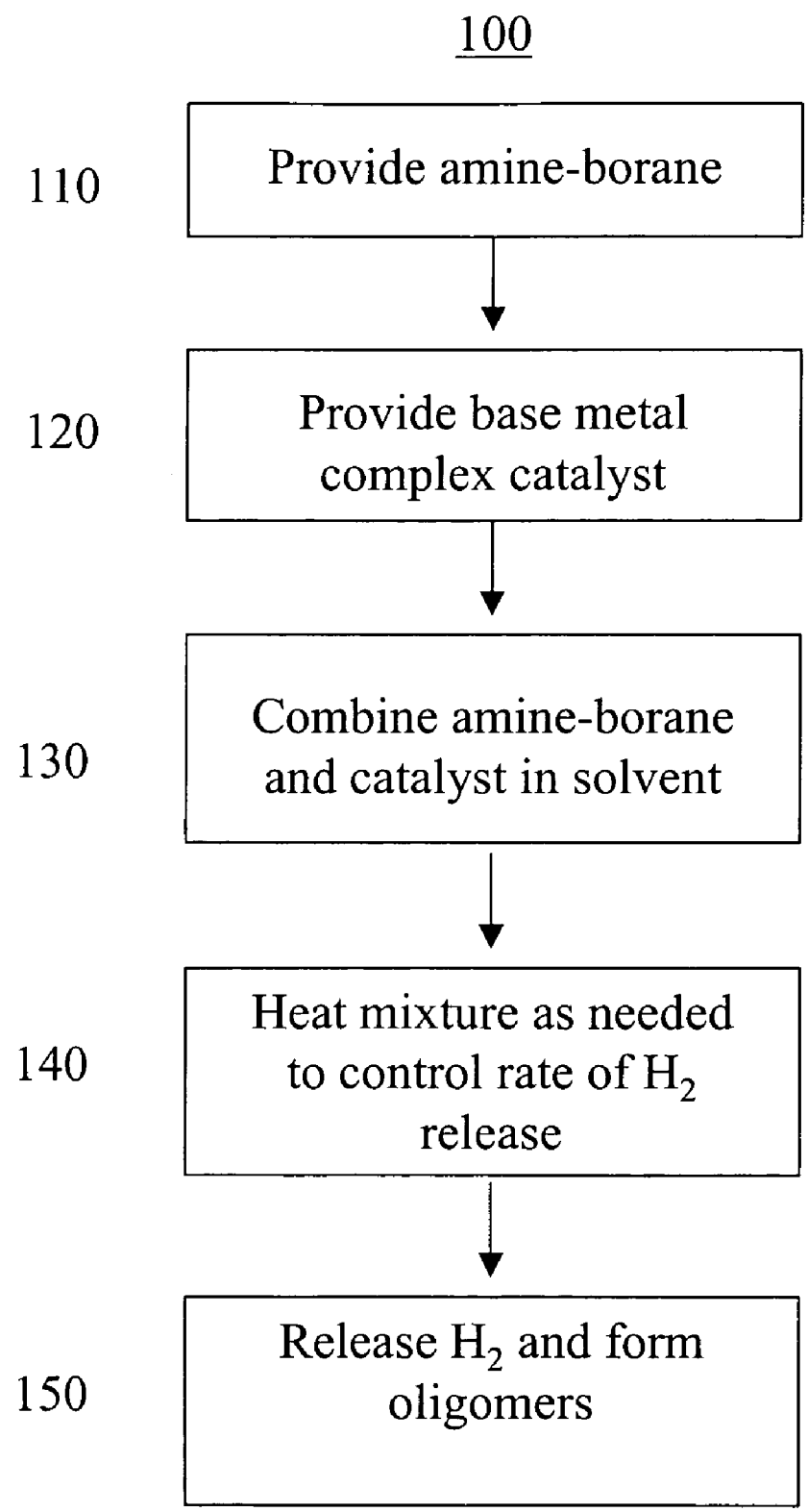

US 7,544,837 B2

BASE METAL DEHYDROGENATION OF AMINE-BORANES

REFERENCE TO PRIOR APPLICATION

This application claims the benefit of U.S. Provisional Application No. 60/733,836, filed Nov. 4, 2005.

STATEMENT REGARDING FEDERAL RIGHTS

This invention was made with government support under Contract No. DE-AC 52-06 NA 25396, awarded by the U.S. Department of Energy. The government has certain rights in the invention.

BACKGROUND OF INVENTION

The invention relates to amine-boranes. More particularly, the invention relates to a method of dehydrogenating amine-boranes. Even more particularly, the invention relates to a method of providing hydrogen for power generation sources, such as fuel cells.

Chemical hydrides for hydrogen storage are being explored as alternatives to high-pressure hydrogen tanks (gas or liquid), sorbents, adsorbed hydrogen, and metal hydride fuels. Chemical hydrides have the potential to be packaged as non-pyrophoric, non-hazardous, solid, or slurried fuels for automotive applications. Hydrogen may then be generated from such hydrides under controlled conditions on-board and on demand. The spent fuel may then be regenerated either on-board or off-board.

Hydrogen storage materials should ideally have high hydrogen content and low molecular weight. Ammonia-borane ($H_3NBH_3$), having a molecular hydrogen storage capacity of 19.6 wt %, is therefore an attractive material for such applications. Because the molecule contains both hydridic and protic hydrogen atoms, it spontaneously loses $H_2$ at temperatures above 80° C. Ultimately, $H_3NBH_3$ can be dehydrogenated completely, forming ceramic BN, but temperatures in excess of 500° C. are required. Thermal decomposition of ammonia-borane in solution initially affords the cyclic oligomers cyclotriborazane ($B_3N_3H_{12}$) and borazine ($B_3N_3H_6$). It has been demonstrated that preparation of $B_3N_3H_6$ from $H_3NBH_3$ on a large scale can be achieved in high yield over 3 hours by simply heating a tetraglyme solution of ammonia-borane. In addition, it has been shown that borazine can be thermally crosslinked at temperatures as low as 70° C. with concomitant $H_2$ evolution.

It is possible to obtain a large amount of hydrogen from $H_3NBH_3$, but low energy (i.e., minimal heat input) methods to utilize this fuel are only just being developed. For example, $H_2$ has been liberated at room temperature from $H_3NBH_3$ and the related species dimethylamine-borane ($HMe_2NBH_3$) by adding precious metal catalysts. For example, select Rh(I) species dehydrocouple $HMe_2NBH_3$ to form $H_2$, along with the cyclic dimer $[Me_2NBH_2]_2$ and acyclic aminoborane polymers. Phosphine-boranes having the general formula $H_2RPBH_3$ (R=H, Ph) also can be dehydrocoupled using metal catalysts to yield acyclic polymers.

Currently, methods of dehydrogenating amine-boranes at low temperature require the use of expensive precious metal catalysts such as rhodium. Therefore, what is needed is a method of dehydrogenating amine-boranes without the use of precious metal catalysts at low temperatures. What is also needed is a metal catalyst for dehydrogenation that can be easily regenerated.

SUMMARY OF INVENTION

The present invention meets these and other needs by providing a method of dehydrogenating an amine-borane using a base metal catalyst. The method generates hydrogen and produces at least one of a $[R^1HN—BHR^2]_m$ oligomer and a $[R^1N—BR^2]_n$ oligomer. The method of dehydrogenating amine-boranes may be used to generate $H_2$ for portable power sources, such as, but not limited to, fuel cells.

Accordingly, one aspect of the invention is to provide a method of dehydrogenating an amine-borane. The method comprises the steps of: providing at least one amine-borane having the formula $R^1H_2N—BH_2R^2$; providing at least one base metal catalyst; and combining the at least one base metal catalyst and the at least one amine-borane, wherein the base metal catalyst reacts with the at least one amine-borane to release hydrogen and yield at least one of a $[R^1HN—BHR^2]_m$ oligomer and a $[R^1N—BR^2]_n$ oligomer.

A second aspect of the invention is to provide a base metal catalyst for dehydrogenating an amine-borane. The base metal catalyst comprises: a base metal, wherein the base metal is a transition metal other than platinum, palladium, rhodium, iridium, osmium, and ruthenium; and at least one ligand bonded to the base metal, wherein the at least one ligand comprises one of oxygen, phosphorus, carbon, nitrogen, sulfur, and combinations thereof.

A third aspect of the invention is to provide a method of producing hydrogen in a fuel cell. The method comprises the steps of: providing at least one amine-borane to the fuel cell, wherein the amine-borane has the formula $R^1H_2N—BH_2R^2$; forming a solution or a slurry of the at least one amine-borane in a solvent; and providing at least one base metal catalyst to the fuel cell, wherein the base metal catalyst comprises a base metal, wherein the base metal is a transition metal other than platinum, palladium, rhodium, iridium, osmium, and ruthenium; and at least one ligand bonded to the base metal, wherein the at least one ligand comprises one of oxygen, phosphorus, carbon, nitrogen, sulfur, and combinations thereof; and combining the solution or slurry with the at least one base metal catalyst, wherein the base metal catalyst reacts with the at least one amine-borane to release hydrogen and yield at least one of a $[R^1HN—BHR^2]_m$ oligomer and a $[R^1N—BR^2]_n$ oligomer.

These and other aspects, advantages, and salient features of the present invention will become apparent from the following detailed description, the accompanying drawings, and the appended claims.

BRIEF DESCRIPTION OF THE DRAWINGS

FIG. 1 is a flow chart for a method of dehydrogenating an amine-borane.

DETAILED DESCRIPTION

In the following description, like reference characters designate like or corresponding parts throughout the several views shown in the figures. It is also understood that terms such as "top," "bottom," "outward," "inward," and the like are words of convenience and are not to be construed as limiting terms. In addition, whenever a group is described as either comprising or consisting of at least one of a group of elements and combinations thereof, it is understood that the group may comprise or consist of any number of those elements recited, either individually or in combination with each other.

Referring to the drawings in general and to FIG. 1 in particular, it will be understood that the illustrations are for the purpose of describing a particular embodiment of the invention and are not intended to limit the invention thereto. A flow chart of a method 100, described herein, of dehydrogenating an amine-borane is shown in FIG. 1. In Step 110, at least one amine-borane having the general formula $R^1H_2N$—$BH_2R^2$ is provided. Each of the groups $R^1$ and $R^2$, independently and at each occurrence, is one of H, an alkyl group, or an aryl group. As described herein, "alkyl" is understood to mean an alkyl group having up to and including 12 carbons. Common examples of such alkyl groups include, but are not limited to, methyl, ethyl, propyl, isopropyl, butyl, s-butyl, t-butyl, isobutyl, pentyl, neopentyl, hexyl, heptyl, isoheptyl, 2-ethylhexyl, cyclohexyl, and octyl groups. Similarly, "aryl" is understood to mean a group defined as a monovalent radical formed conceptually by removal of a hydrogen atom from a hydrocarbon that is structurally composed entirely of one or more benzene rings. Common examples of such hydrocarbons include, but are not limited to, benzene, biphenyl, terphenyl, naphthalene, phenyl naphthalene, anthracene, phenanthrene, and naphthylbenzene. Non-limiting examples of such amine-boranes include benzylamine-borane, methylamine-borane and ethylenediamine-bis(borane).

In one embodiment, each of $R^1$ and $R^2$ are hydrogen; i.e., the amine borane is ammonia-borane ($H_3NBH_3$). For applications such as hydrogen generation in fuel cells, ammonia-borane is the preferred amine-borane, due to its high hydrogen density. The at least one amine-borane is typically dissolved or slurried in a polar, non-protic solvent. Non-limiting examples of such solvents include toluene, chlorinated solvents such as methylene chloride and 1,2-dichlorobenzene, and ethereal solvents such as tetrahydrofuran (THF), 1,2-dimethoxyethane, diglyme, and polyethylene glycol dimethyl ether. Such solvents may be used either individually or in combination with each other.

At least one base metal catalyst is provided in Step 120. As used herein, the term "base metal" is understood to include transition metals other than platinum, palladium, rhodium, iridium, osmium, and ruthenium. In one embodiment, the base metal is selected from the group consisting of manganese, iron, cobalt, nickel, and copper. In one embodiment, the base metal catalyst is a base metal complex in which at least one ligand is bonded to the base metal. The at least one ligand may include at least one of oxygen, nitrogen, carbon, phosphorus, sulfur, and combinations thereof. The at least one ligand may include a multidentate ligand. Non-limiting examples of active catalysts include tetrakis(trimethylphosphine) nickel, bis(N-heterocyclic carbene) nickel, bis(dimethylphosphino)ethane iron dichloride, and N-heterocyclic carbene copper chloride. The base metal catalyst may be slurried or dissolved in solution with the same solvent as that used to dissolve or slurry the at least one amine-borane. In another embodiment, the base metal catalyst may be a supported catalyst, such as, for example, iron chloride coordinated to polymer-bound triphenylphosphine.

The at least one amine-borane and the at least one base metal catalyst are combined in a solvent in Step 130, and the mixture is heated to control the rate of hydrogen release (Step 140). The base metal catalyst reacts with the amine-borane to release hydrogen and yield at least one oligomer having the general formula $[R^1HN—BHR^2]_m$ or $[R^1N—BR^2]_n$ (Step 150). The at least one oligomer produced by the reaction may include cyclic oligomers, acyclic oligomers, or both cyclic and acyclic oligomers. In one embodiment, the at least one base metal catalyst is added to the solution or slurry containing the at least one amine-borane. The combined base metal catalyst and solution or slurry are gently heated up to about 60° C. In one embodiment, the combined base metal catalyst and solution or slurry are heated up to about 80° C. Hydrogen evolves upon such heating, and the polymeric precipitate forms after several hours.

The use of the base metal catalysts described herein for dehydrogenation of amine-boranes permits hydrogen evolution to take place at temperatures that are lower than those used in other processes. For example, dehydrogenation by thermal decomposition takes place very slowly at about 80° C. In addition, variation of the ligands on the base metal catalysts provides some control over the formation of acyclic oligomers as opposed to formation of volatile cyclic products. Such volatile cyclic products, including cyclotriborazane ($B_3N_3H_{12}$) and borazine ($B_3N_3H_6$), may interfere with fuel cell catalysts. Moreover, acyclic oligomers are less stable than cyclic products and therefore require less energy to regenerate. Base metal catalysts also provide greater processing flexibility than precious metal catalysts, as the base metals are easier to separate or redissolve than the precious metals.

When $R^1=R^2=H$, further dehydrogenation of the $[R^1HN—BHR^2]_n$ oligomer may be achieved by either heating the precipitate in a range from about 25° C. to about 200° C. to extract additional $H_2$ and yield $[R^1N—BR_2]_n$. Additional hydrogen may then be extracted by further heating, yielding $BNH_x$. In either case, the residue may be used to regenerate amine-borane.

The following examples illustrate the features and advantages of the invention and are not in any way intended to limit the invention thereto.

EXAMPLE 1

Preparation of Amine-Borane

Amine-borane was prepared as follows. In one method, anhydrous ammonia gas was bubbled through a 1 M solution of $BH_3$.THF in THF for 1 hour at 20° C. Alternatively, equimolar amounts of a 1 M solution of $BH_3$.THF in THF and a 0.5 M solution of $NH_3$ in dioxane were combined at 20° C. Ammonia-borane was purified by precipitation from the reaction mixture using hexane and subsequent recrystallization from THF/$Et_2O$.

EXAMPLE 2

Thermal Dehydrogenation of Ammonia-Borane without a Catalyst

A solution of 14 mg ammonia-borane (0.46 mmol) in 0.5 mL of 1,2-dimethoxyethane and 1 mL of $C_6D_6$ was heated at 60° C. for 19 hr. Conversion was ca. 60% to a 3:1 mixture of $[H_2NBH_2]_n$ and $[HNBH]_3$.

EXAMPLE 3

Iron P-Ligand Complex-Catalyzed Dehydrogenation of Ammonia-Borane

A solution of $Fe(Et_2PCH_2CH_2PEt_2)(PMe_3)_3$ (6.7 mg, 0.02 mmol) in $C_6D_6$ was added to 2.5 mg (0.08 mmol) of solid ammonia-borane ($H_3N—BH_3$) at room temperature. Reaction progress was monitored by $^1$H and $^{11}$B NMR over time. After several days a mixture of $[H_2NBH_2]_n$ and $[HNBH]_3$ was obtained.

EXAMPLE 4

Kinetics of Nickel C-Ligand Complex-Catalyzed Dehydrogenation of Ammonia-Borane A solution of 8 mg (0.03 mmol) of Ni(1,5-cyclooctadiene)$_2$ and 18 mg (0.06 mmol) of N-heterocyclic carbene 1,3,4-triphenyl-4,5-dihydro-1H-1,2,4-triazol-5-ylidene in 0.5 mL of $C_6D_6$ was added to a solution of 18 mg (0.6 mmol) ammonia-borane in 1 mL of 1,2-dimethoxyethane. The solution was heated at 60° C. and monitored by B-11 NMR at intervals of 10, 20, 44, 60 and 80 min. to determine kinetics of consumption of ammonia-borane.

EXAMPLE 5

Hydrogen Measurement of Nickel C-Ligand Complex-Catalyzed Dehydrogenation of Ammonia-Borane A solution of 8 mg (0.03 mmol) of Ni(1,5-cyclooctadiene)$_2$ and 18 mg (0.06 mmol) of N-heterocyclic carbene 1,3,4-triphenyl-4,5-dihydro-1H-1,2,4-triazol-5-ylidene in 1 mL of $C_6D_6$ was added to a solution of 10 mg (0.3 mmol) ammonia-borane in 2 mL of 1,2-dimethoxyethane. The reaction vessel was attached to a gas burette and heated at 60° C. for 3 hours, after which time 28 mL of a possible 31 mL of hydrogen (based on 3 equivalents per ammonia-borane) were collected.

EXAMPLE 6

Nickel C-Ligand Catalyzed Dehydrogenation of Isobutylamine-Borane

To 8 mg (0.03 mmol) of Ni(1,5-cyclooctadiene)$_2$ and 26 mg (0.09 mmol) of N-heterocyclic carbene 1,3,4-triphenyl-4,5-dihydro-1H-1,2,4-triazol-5-ylidene was added $C_6D_6$. The resulting deep purple solution was added to 13 mg (0.15 mmol) of isobutylamine-borane (iBuH$_2$N-BH$_3$). The homogeneous mixture was heated to 60° C. for 12 hours. Monitoring the reaction by $^1$H and $^{11}$B NMR indicated formation of $[iBuHNBH_2]_m$ and $[iBuNBH]_n$ oligomers.

EXAMPLE 6

Nickel O-Ligand Complex-Catalyzed Dehydrogenation of Isobutylamine-Borane

A solution of isobutylamine-borane (10 mg, 0.12 mmol) in 1 mL of $C_6D_6$ was added to Ni (acac)$_2$ (6 mg, 0.02 mmol) at room temperature. Reaction progress was monitored by $^1$H and $^{11}$B NMR over time. After 36 hours, a mixture of $[H(i-Bu)NBH_2]_n$ and $[(i-Bu)NBH]_3$ was obtained.

EXAMPLE 7

Copper C-Ligand Catalyzed Dehydrogenation of Dimethylamine-Borane

Solid dimethylamine-borane (Me$_2$HN-BH$_3$) (5 mg, 0.08 mmol) was dissolved in $C_6D_6$. This solution was added to 11 mg (0.02 mmol, ~20 mol %) of (carbene)CuCl (carbene is 2,5-(2,6-diisopropylphenyl)imidazolidene). Vigorous gas evolution ensued. Reaction progress was monitored by $^1$H and $^{11}$B NMR. Initial formation of $[Me_2NBH_2]_n$ where n=1, 2, and 3 was followed by conversion to the cyclic dimer $[Me_2NBH_2]_2$.

EXAMPLE 9

Manganese-C-Ligand Complex-Catalyzed Dehydrogenation of Dimethylamine-Borane A solution of (C$_5$H$_5$)Mn(CO)$_3$ (5 mg, 0.025 mmol) and dimethylamine-borane (7 mg, 0.12 mmol) in 1 mL of $C_6D_6$ was heated at 60° C. for two days to give ca. 80% conversion to $[Me_2NBH_2]_2$.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

The invention claimed is:

1. A method of thermolytically dehydrogenating an amine-borane, the method comprising the steps of:
    a) providing at least one amine-borane, wherein the amine-borane has the formula R$^1$H$_2$N—BH$_2$R$^2$; where R$^1$ and R$^2$ are independently one of H, an alkyl group, or an aryl group;
    b) providing at least one base metal catalyst selected from the group consisting of manganese, iron, cobalt, nickel, and copper and combinations thereof;
    c) combining the at least one base metal catalyst and the at least one amine-borane, wherein the base metal catalyst reacts with the at least one amine-borane to release hydrogen and yield at least one of an aminoborane oligomer and an iminoborane oligomer; and
    d) heating at least one of the aminoborane oligomer and the iminoborane oligomer to a predetermined temperature.

2. The method according to claim 1, wherein the step of combining the at least one base metal catalyst and the at least one amine-borane to form a catalytic initiator comprises:
    a) forming a solution or a slurry comprising the at least one amine-borane in a solvent;
    b) combining the at least one base metal catalyst with one of the solution and the slurry; and
    c) heating the at least one base metal catalyst combined with one of the solution and the slurry to a temperature of up to about 80° C.

3. The method according to claim 2, wherein the step of heating the at least one base metal catalyst combined with the solution or the slurry to a temperature of up to about 80° C. comprises healing the at least one base metal catalyst combined with one of the solution and the slurry up to about 60° C.

4. The method according to claim 2, wherein the solvent is selected from the group of solvents consisting of toluene, chlorinated solvents, and ethereal solvents.

5. The method according to claim 4, wherein the chlorinated solvent is one of methylene chloride, 1,2-dichlorobenzene, and combinations thereof.

6. The method according to claim 4, wherein the ethereal solvent is one of tetrahydrofuran, 1,2-dimethoxyethane, diglyme, polyethylene glycol dimethyl ether, and combinations thereof.

7. The method according to claim 1, wherein the at least one base metal catalyst further includes at least one ligand bonded to the base metal, wherein the at least one ligand comprises one of oxygen, phosphorus, carbon, nitrogen sulfur, and combinations thereof.

8. The method according to claim 7, wherein the at least one ligand includes a multidentate ligand.

9. The method according to claim 7, wherein the at least one base metal catalyst is selected from the group consisting of tetrakis(trimethylphosphine) nickel, bis(N-heterocyclic carbene) nickel, bis(dimethylphosphino)ethane iron dichloride, and N-heterocyclic carbene copper chloride.

10. The method according to claim 1, wherein each of $R^1$ and $R^2$, independently and at each occurrence, is one of hydrogen, an alkyl group, and an aryl group.

11. The method according to claim 10, wherein each of $R^1$ and $R^2$, independently and at each occurrence, is hydrogen.

12. The method according to claim 1, wherein the predetermined temperature is in a range from about 80° C. to about 200° C.

13. The method according to claim 1, wherein at least one of the aminoborane oligomer and the iminoborane oligomer comprises at least one of an acyclic oligomer and a cyclic oligomer.

* * * * *